(12) United States Patent
Oliveira

(10) Patent No.: US 10,537,101 B2
(45) Date of Patent: *Jan. 21, 2020

(54) METHOD FOR REDUCING PHYTOTOXICITY OF FUNGICIDES

(71) Applicant: UPL LTD., Mumbai (IN)

(72) Inventor: Gilson Aparecido Hermenegildo de Oliveira, Campinas (BR)

(73) Assignee: UPL LTD., West Bengal (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/535,290

(22) PCT Filed: Dec. 10, 2015

(86) PCT No.: PCT/BR2015/050241
§ 371 (c)(1),
(2) Date: Jun. 12, 2017

(87) PCT Pub. No.: WO2016/090446
PCT Pub. Date: Jun. 16, 2016

(65) Prior Publication Data
US 2017/0367337 A1 Dec. 28, 2017

(30) Foreign Application Priority Data
Dec. 12, 2014 (BR) .......................... 1020140312528

(51) Int. Cl.
*A01N 43/653* (2006.01)
*A01N 47/14* (2006.01)
*A01N 25/32* (2006.01)

(52) U.S. Cl.
CPC ........... *A01N 43/653* (2013.01); *A01N 25/32* (2013.01); *A01N 47/14* (2013.01)

(58) Field of Classification Search
CPC ....... A01N 25/32; A01N 43/653; A01N 47/14
See application file for complete search history.

(56) References Cited

U.S. PATENT DOCUMENTS

| | | | | |
|---|---|---|---|---|
| 4,394,966 A * | 7/1983 | Snyder | .................. | B01F 5/0212 239/127 |
| 4,886,825 A | 12/1989 | Ruess et al. | | |
| 9,788,544 B2 * | 10/2017 | Oliveira | .................. | A01N 47/24 |
| 2014/0378514 A1 * | 12/2014 | Krieg | ...................... | A01N 43/40 514/357 |
| 2017/0332637 A1 | 11/2017 | Oliveira et al. | | |

FOREIGN PATENT DOCUMENTS

WO WO 2007/093535 8/2007

OTHER PUBLICATIONS

Bayer (SeedQuest, News Section, May 18, 2005) (Year: 2005).*
Grigolli (J. F. J. Apresentagao de Resultados—Fundagao MS. Mato Grosso do Sul, 2014, English translation) (Year: 2014).*
Esker, http://corn.agrononny.wisc.edu/Managennent/pdfs/A3878.pdf, 2008 (Year: 2008).*
PennstateExtension (Fungicides, Herbicides and Insecticides, Feb. 1, 2001). (Year: 2001).*
Rush, Jun. 22, 2018, p. 1 (https://www.fginsight.conn/news/news/registration-sought-for-new-strobilurin-fungicide-63958) (Year: 2018).*
Grigolli, J.F.J. "Ocorrência e controle das principais pragas e doenças da soja", Apresentaçao de resultados—Fundaçao MS. 2014. Available in: http://www.fundacaoms.org.br/base/www/fundacaoms.org.br/media/attachments/84/84/53a44ebbef004da589c1b44eab592a62ac642b31ebcb3_palestra_fernando_lurca_fitossanidade.pdf.
Delaro(TM) 325 SC Fungicide; U.S. Environmental Protection Agency, Acceptance of Label Amendment, dated Jan. 23, 2018, 21 pages.
Godoy, Claudia Vieira; "Brazilian Soybean Pest Management and Threats to its Sustainability"; 6 pages; https://www.researchgate.net/publication/279969388; Uploaded Sep. 9, 2016; published Jun. 2015.
Godoy, Claudia Vieira; Changes in Performance of SBR Fungicides Over the Years and New Management Strategies Adopted in Brazil; ResearchGate;18 pages; https://www.researchgate.net/publication/265235129; 2018.
Godoy, Claudia Vieira; "Risk and Management of Fungicide Resistance in the Asian Soybean Rust Fungus Phakopsora Pachyrhizi"; 10 pages; https://www.researchgate.net/publication/285130302; Uploaded Apr. 1, 2016; published Dec. 2011.
FRAC Code List (c)*2018: Fungicides Sorted by Mode of Action (Including FRAC Code Numbering).
Robinson et al.; "Winter Wheat (*Triticum aestivum* L.) Tolerance to Mixtures of Herbicides and Fungicides Applied at Different Times"; Can. J. Plant Sci.; (2013); 93; pp. 491-501.

* cited by examiner

*Primary Examiner* — Umamaheswari Ramachandran
(74) *Attorney, Agent, or Firm* — Cantor Colburn LLP

(57) ABSTRACT

The present invention relates to a method for reducing the phytotoxicity of systemic fungicides, mainly triazoles, in susceptible cultivars, mainly soy cultivars. The present method makes it unnecessary to develop new diversified fungicide formulations and to add specific substances to reduce the toxicity of these products.

3 Claims, No Drawings

METHOD FOR REDUCING PHYTOTOXICITY OF FUNGICIDES

TECHNICAL FIELD OF THE INVENTION

The present invention relates to a method for reducing the phytotoxicity of systemic fungicides, especially triazoles in susceptible cultivars of soybeans, among others. With this method it is unnecessary to innovate in diverse fungicide formulations and to add specific substances to alleviate the toxicity of systemic fungicides, especially triazoles.

BACKGROUND OF THE INVENTION

Fungicides are chemical compounds that kill or inhibit the growth of fungi and their spores. The use of fungicides to effectively control plant diseases have become essential to the farming system in recent decades, since the diseases in cultivars reduce in about 20% the world food production.

Due to its relatively low cost and effectiveness in the elimination of the diseases, fungicides have become the preferred means of control of plant diseases caused by fungi. However, it is known that its continued use and on a large scale leads to the emergence of new strains of fungi, which become resistant to the commercial products available. This can be exemplified by what is happening with the resistance of Phakopsora pachyrhizi (Pp), the causal agent of soybean rust, to the DMI (demethylation inhibitors), QoI (quinone outside inhibitors) SDHI, and mixtures thereof.

Nevertheless, studies on the negative effects of fungicides to alter or inhibit the metabolic activity of healthy plants, as well as the effects of the application of some fungicides on photosynthesis, pigments content, growth and changes in the reproductive organs are still under explored. Some available data reported changes in CO2 assimilation and in the photosynthetic efficiency of the plant.

With respect to the soybean culture, it is known that the fungicides used on a large scale belong to two chemical groups, with site specific mechanism of action, which are: triazoles or DMIs; and strobilurins, or QoIs. More recently a third chemical group started to being used, namely, the SDHI (succinate dehydrogenase enzyme inhibitors). The combination of the DMIs with QoIs has been used in more than 12 crops for the control of the FAS. Additionally, reducing the sensitivity of Phakopsora pachyrhizi (Pp) to the DMI burdened the QoIs antifungal action in the mixtures.

From the 2012/13 crop it was observed that Pp had its sensitivity reduced to the mixtures of DMIs+QoIs.

With respect to the triazoles (DMI), it is known that its action mechanism aims at inhibiting a specific enzyme, C14-demethylase, which plays a crucial role in sterol production. Sterols, such as ergosterol, are integral parts of the structure and function of the membranes, becoming essential elements in its synthesis, and after the germination of the spores.

Although DMIs do not inhibit the germination of spores, they begin their antifungal action shortly after germination (elongation of germ tube), that is, the phase of the fungal life cycle that requires the formation of new membranes with consequent sterol production. The formation of such other structures that follow the elongation process of the germ tube, involves the infection structures like appressorium and penetration tube. All require the formation of new membranes and consequently the raw material for the sterols. At the end, the antifugal activity results in the prevention of fungal tissue penetration of the hosts and the cessation of the infectious process. Therefore, triazoles cause abnormal growth of fungi and their eventual death, which is quite satisfactory.

It should be noted that each triazole compound (DMI) works slightly differently from the others, due to the use of different biochemical pathways in sterol synthesis. Although there are similarities between them, there are major differences in the spectrum of action of each. It is known of reports of injuries in soybean cultivars associated with the application of DMIs, especially tebuconazole and prothioconazole. A known problem is the phytotoxicity of these fungicides such as, for example, tebuconazole, which usually occurs when spraying is done in a hot and dry environment and with the presence of surfactants added to the fungicide, which further increases the intensity of the injury.

In Brazil, little is known about the reaction of the Brazilian cultivars to triazoles. What is known is that the application of mostly systemic fungicides especially triazoles with spray in soybean crops, results in bands of leaves with yellowing, light discoloration, death and detachment of the internervurais spaces of soybean leaflets. The soybean leaves also have symptoms which are mistaken with nutrient deficiency, secondary symptoms of disease and phytotoxicity of external chemical agents (such as, for example, triazoles fungicides). This type of leaf symptoms receives the popular name in Brazil of carijó leaf. It should be noted that the phytotoxicity occurs only at the top of the crop canopy, in the areas covered with the largest volume of product used in the spraying. The lower leaves have normal green color and the stem without evidence of injury. Generally, the toxicity of systemic fungicides, especially triazoles, appears in crops under special conditions. For example, triazole fungicides can be used in soybean crops, with the proviso to avoid application to cultivars more sensitive to fungicides, or to avoid application at elevated temperatures above 35° C. (or in the hottest time of the day) and water stress (caused by drought). The most intense symptoms of phytotoxicity are observed in the areas of overlap of the fungicide spray bar and maneuver places to return. The areas where the fungicide was not applied have superior leaves of normal green color, without the characteristic phytotoxicity. Under plant growth and normal environmental conditions there is no presence of phytotoxicity on the leaves. This injury reduces the photosynthetic potential of the top of the canopy, which receives the largest amount of solar radiation. The production is a function of the duration of green healthy leaf area and the absorbed radiation.

The state of art to date has not solved the problems described here, so much that the nearest patent literature does not address the subject. As an example we can mention:

International application WO2007/028388 entitled "Method of reducing phytotoxicity on plants susceptible to systemic fungicides Mainly triazoles" which discloses that triazole fungicides can be applied to a cultivar susceptible to triazole fungicides, which is incorporated via a formulation that comprises certain solvents, which reduces or eliminates the phytotoxicity of the fungicide to said cultivar. As can be seen, this invention uses solvents in the formulation, which is a major problem for the producer when using the fungicide formulated in the soybean crop.

In order to solve the technique problem, the present invention describes a method aimed at reducing the phytotoxicity of systemic fungicides, especially triazoles in susceptible cultivars of soybeans, among others. The use of the method of the present invention allow the safe use of systemic fungicides, especially triazoles, in all cultures.

SUMMARY OF THE INVENTION

The present invention introduces in the Brazilian production system a method for reducing the phytotoxicity of systemic fungicides, especially triazoles, such as tebuconazole and prothioconazole in any crops.

OBJECTS OF THE INVENTION

It is the object of the present invention to reduce the phytotoxicity of systemic fungicides, especially triazoles, such as tebuconazole and prothioconazole, in cultures, more specifically in soybean cultivars.

DETAILED DESCRIPTION OF THE INVENTION

In order to solve one of the problems encountered in the state of art, the present invention developed a method for reducing the phytotoxicity of triazoles fungicides in soybean cultivars. Although the triazoles, such as tebuconazole and prothioconazole, are fungicides commonly used in the control of fungal diseases on soybean crops, they are also causing more toxic effect on plants (phytotoxicity) even at normal doses used for the control of diseases. In the specific case of tebuconazole, both the EC and SC formulations can cause serious injuries in plants; however, in soybean crops, which causes more injury is the EC.

The present invention solves the problem of tebuconazole with the mixture thereof with a multi site fungicide, especially a dithiocarbamate, specifically mancozeb, which has the purpose of increasing the tolerance to the triazoles fungicides. Therefore, the present invention enables the safe use of triazoles fungicides, especially tebuconazole and prothioconazole, in all soybean cultivars. The process consists of:

add the spray tank, mancozeb (manganese ethylene bis (dithiocarbamate)+Zn) in an amount ranging from 1.0 kg/ha and 5.0 kg/ha, preferably 1.0 to 4.0 kg/ha, more preferably between 1.0 and 3.0 kg/ha, together with the fungicide (mixture of prefab "DMI+QoI" or "SDHI+DMI"); trigger the spray tank agitator; and once the syrup is homogenized, apply the syrup in the soybean crop.

The advantage of the method of the present invention is to use the multi site fungicide mancozeb, since so far there are not known cases of fungi resistant to it. The mancozeb is shown therefore as broad-spectrum fungicide highly important for eliminating undesirable phytotoxicity on soybean caused by triazoles fungicides, more precisely by the tebuconazole and prothioconazole. It should be noted that mancozeb has never before been used for this purpose.

Therefore, the present invention, despite being represented by an extremely simple method, it should be seen as innovative and very important for the soybean crop sustainability in Brazil and worldwide. This is because this method has never been used to fight phytotoxicity in crops (this includes the soybean culture).

It will be readily understood by those skilled in the art that modifications can be made herein without thereby departing from the concepts set forth in the above description. These modifications are to be considered comprised by the scope of the present invention.

The invention claimed is:

1. A method of reducing phytotoxicity of a fungicidal combination consisting of tebuconazole or prothioconazole and a strobilurin fungicide in soybean cultivars, the method comprising:
    (i) adding to a spray tank 1.0 kg/ha to 5.0 kg/ha of mancozeb and premixed tebuconazole or prothioconazole and strobilurin fungicide;
    (ii) triggering the spray tank agitator to produce a homogenized syrup; and
    (iii) applying the homogenized syrup to top leaves of a soybean crop,
    wherein adding mancozeb to the fungicidal combination consisting of tebuconazole or prothioconazole and a strobilurin fungicide decreases the phytotoxicity of the tebuconazole or prothioconazole to the soybean crop in comparison to a method lacking adding mancozeb.

2. The method according to claim 1, wherein the mancozeb is added in an amount of 1.0 to 4.0 kg/ha.

3. The method according to claim 1, wherein the mancozeb is added in an amount ranging from between 1.0 and 3.0 kg/ha.

* * * * *